United States Patent [19]

Yagami et al.

[11] Patent Number: 5,546,947
[45] Date of Patent: Aug. 20, 1996

[54] ULTRASONIC ENDOPROBE

[75] Inventors: Hiroyuki Yagami; Naoto Sato; Hideaki Yamashita; Satoshi Nakagawa; Jun Maekawa, all of Fujinomiya, Japan

[73] Assignee: Terumo Kabushiki Kaisha, Tokyo, Japan

[21] Appl. No.: 312,964

[22] Filed: Sep. 30, 1994

[30] Foreign Application Priority Data

Sep. 30, 1993 [JP] Japan .................................. 5-245335
Dec. 3, 1993 [JP] Japan .................................. 5-304143
Mar. 18, 1994 [JP] Japan .................................. 6-048302
Mar. 31, 1994 [JP] Japan .................................. 6-063828

[51] Int. Cl.$^6$ ........................................................ A61B 8/12
[52] U.S. Cl. ................................................... 128/662.06
[58] Field of Search .................... 128/660.03, 662.03, 128/662.06, 660.1, 772; 604/22; 606/159, 169

[56] References Cited

U.S. PATENT DOCUMENTS 3,913,565 10/1975 Kawahara ........................... 128/2 M
5,168,878 12/1992 Takano ............................. 128/662.06
5,255,681 10/1993 Ishimura et al. ................. 128/660.09
5,312,427 5/1994 Shturman ............................ 606/159
5,348,017 9/1994 Thornton et al. ................. 128/662.06
5,368,035 11/1994 Hamm et al. ..................... 128/662.06
5,377,682 1/1995 Ueno et al. .................. 128/662.06 X
5,397,306 3/1995 Nobuyoshi et al. ................... 604/96
5,437,282 8/1995 Koger et al. ..................... 128/662.06

*Primary Examiner*—Francis Jaworski
*Attorney, Agent, or Firm*—Burns, Doane, Swecker & Mathis, L.L.P.

[57] ABSTRACT

One ultrasonic endoprobe of this invention has a tubular member formed of a superelastic metal tube and a resin cover covering the outside surface of the superelastic metal tube. An inner assembly comprising an ultrasonic transducer is housed in the tubular member. Another ultrasonic endoprobe of this invention has a composite tubular member formed of a coil, a braid covering the outside surface of the coil, and an outer cover covering the outside surface of the braid. An inner assembly comprising an ultrasonic transducer is housed in the composite tubular member. The ultrasonic endoprobe of this invention has a very small diameter, a high flexibility, a high durability, and a higt torque-transmissibility.

11 Claims, 7 Drawing Sheets

FIG. 8
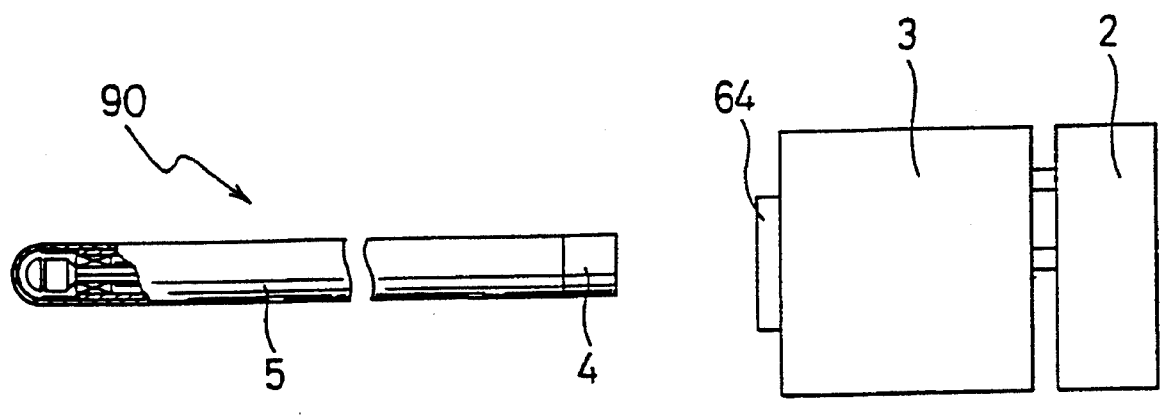
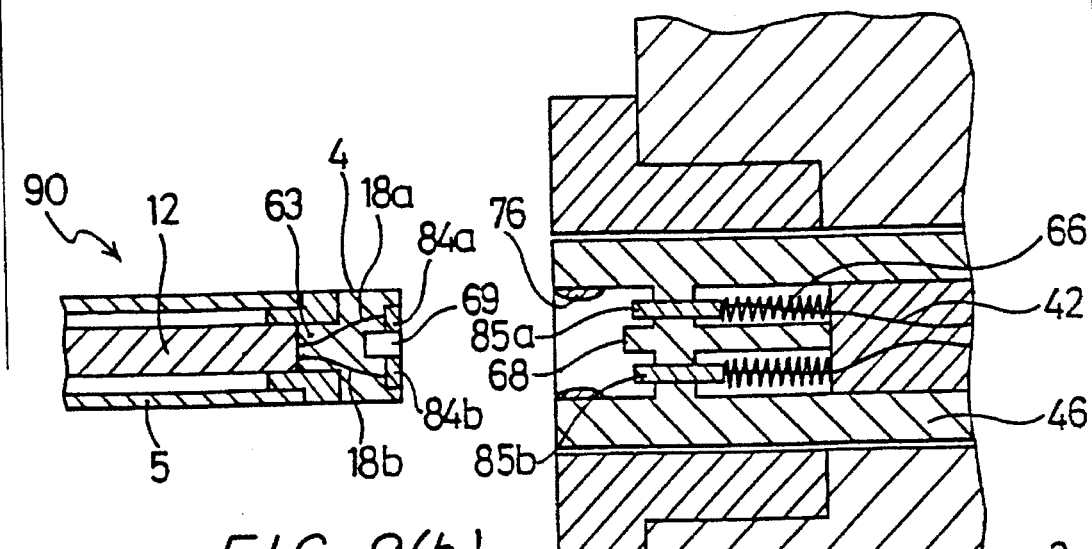
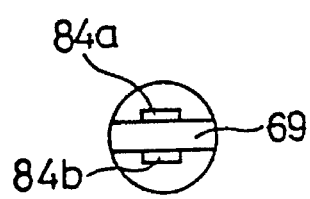

ULTRASONIC ENDOPROBE

This invention relates to an ultrasonic endoprobe which is inserted into a hollow organ or part of a living body such as the digestive tract, urethra or blood vessel or a body cavity such as abdominal cavity and allows close examination of the desired part of the living body by means of ultrasonic waves.

In recent years, it becomes possible to examine almost any part of the human body by visual examination using an ultrasonic diagnostic apparatus. Along with this advance of the ultrasonic diagnosis, various types of ultrasonic probes for producing images of organs from outside the body were put to practical use.

Today, much closer examination became possible by inserting a transrectum probe, transvaginal probe or transesophagus probe into a diseased part. Probes of such a small diameter that can be inserted into an endoscope or into a blood vessel were also developed. Examination of the stomach, colecyst and pancreas by combined use of these small-diameter probes with an endoscopy and that of cross sections of the coronary artery by using them in combination with photofluorography are being attempted.

For a thin probe intended to insert into the body, an inner assembly comprising an ultrasonic transducer, electric conductors for connecting the ultrasonic transducer and the external unit, a member for transmitting rotation or reciprocating motion to the ultrasonic transducer (drive shaft) is encased in a tubular member of the probe. Therefore, the tubular member must have a sufficiently large inside diameter required to accommodate the inner assembly, having a small outside diameter for insertion into the body. The tubular member also must have a sufficiently high flexibility, durability, and motion transmitting capability so that the probe can be easily positioned at the desired part of the body and manipulated for operation. With these conflicting requests, further reduction of the outside diameter of the tubular member is needed to insert a probe into very small blood vessels such as the coronary artery.

Flexible synthetic resin tubes and stainless steel tubes are conventionally used for the tubular member of an ultrasonic probe. However, there are problems with synthetic resin tubes that they are prone to bend at acute angles or flatten, thereby stopping the proper operation of the drive shaft and that they need a comparatively greater wall thickness and hence reduction of the outside diameter is difficult. On the other hand, stainless steel tubes do not flatten, but they lack the flexibility and the durability against repeated bending. Further, because of their low elastic limit, a probe with a stainless steel tube is prone to be bent over the elastic limit of the stainless steel tube and meander, causing a damage to the wall of blood vessels or deteriorating the produced images.

Therefore, the object of this invention is to provide an improved ultrasonic endoprobe and intra-body measurement catheter which have a very small outside diameter and a high motion transmitting capability and thereby can solve the above problems of conventional probes.

SUMMARY OF THE INVENTION

One ultrasonic endoprobe of this invention has a tubular member entirely or partly formed of a superelastic metal tube and a resin cover covering the outside surface of the superelastic metal tube. An inner assembly comprising an ultrasonic transducer is housed in the tubular member.

Another ultrasonic endoprobe of this invention has a composite tubular member formed of a coil, a braid covering an outside surface of the coil, and an outer cover covering the outside surface of the braid. An inner assembly comprises an ultrasonic transducer housed in the composite tubular member, electric conductors attached to the ultrasonic transducer and a drive shaft for moving the ultrasonic transducer.

The intra-body measurement catheter of this invention comprises a catheter tube; a sensor assembly which is housed in the distal end portion of the catheter tube and provided with a sensor; a torque transmitting member which extends inside the catheter tube from the proximal end to the distal end of the catheter tube; and two or more electric conductors for transmitting signals to and from the sensor of the sensor assembly. The electric conductors are bonded on the outside surface of said torque transmitting member.

BRIEF DESCRIPTION OF THE DRAWINGS

FIG. 8 is a side view of another embodiment of the ultrasonic endoprobe of this invention and the external unit.

FIG. 9 (a) is a sectional view which shows the structure for connection of the ultrasonic endoprobe and the external unit shown in FIG. 8.

FIG. 9 (b) is a rear view of the connector of the ultrasonic endoprobe shown in FIG. 8.

DETAILED DESCRIPTION OF PREFERRED EMBODIMENTS

Figure 1:
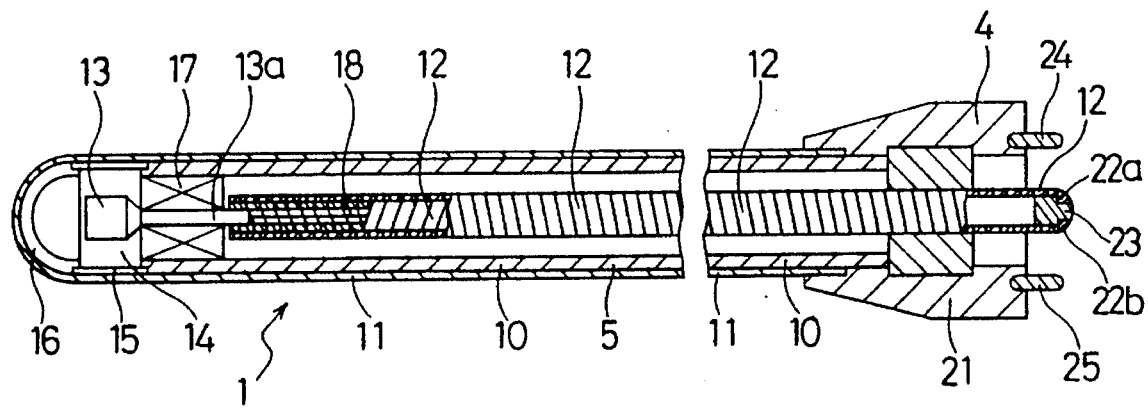
FIG. 1 is a sectional view of an embodiment of the ultrasonic endoprobe of this invention.

The ultrasonic endoprobe of this invention is described below referring to the drawings.

FIG. 1 is a longitudinal sectional view of an embodiment of the ultrasonic endoprobe of this invention, which is an ultrasonic probe of the radial scan type.

Figure 5:
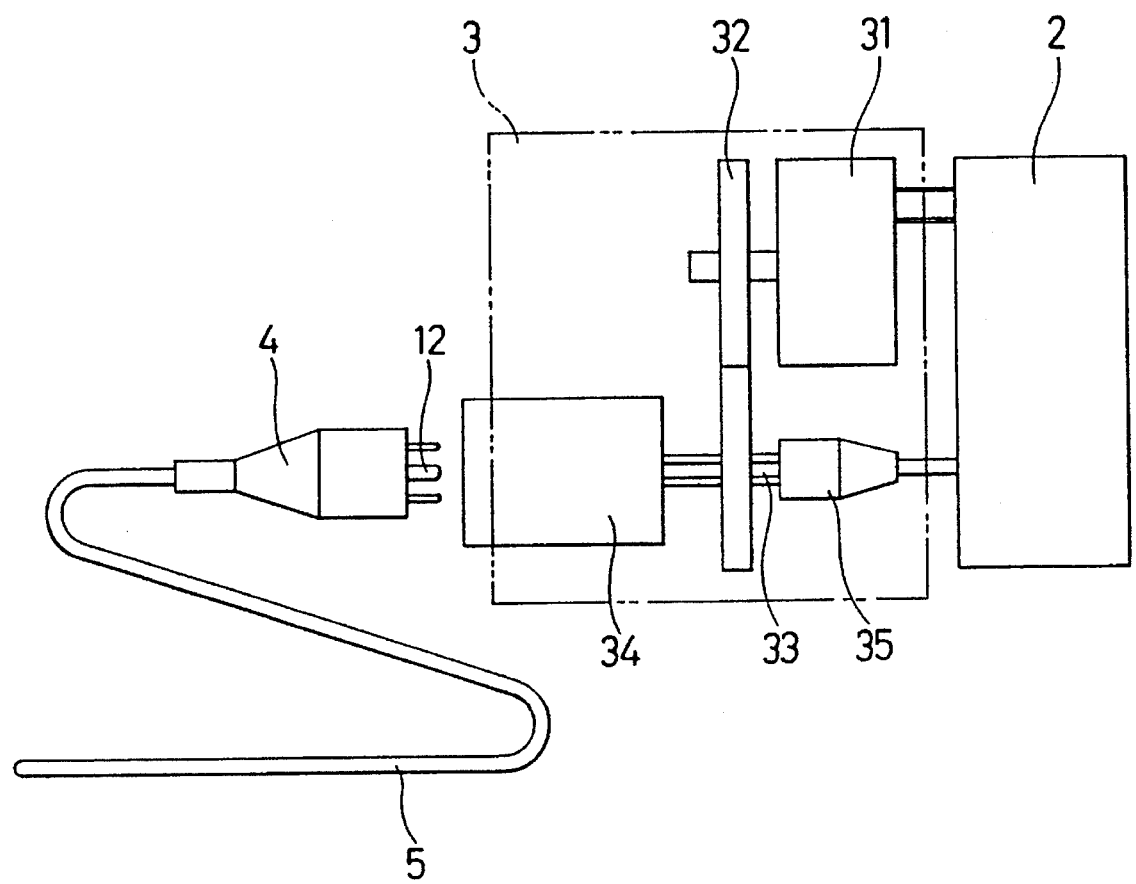
FIG. 5 is a general diagram of an intra-body ultrasonic diagnostic apparatus using the ultrasonic endoprobe of this invention.

FIG. 5 is a general diagram of an intra-body ultrasonic diagnostic apparatus using the ultrasonic endoprobe of this invention. As shown from FIG. 5, the intra-body ultrasonic diagnostic apparatus comprises an ultrasonic endoprobe 1 which is an embodiment of this invention, a main unit 2 of the ultrasonic diagnostic apparatus, and a motor unit 3. The main unit 2 and the motor unit 3 may be conventional ones.

As shown in FIG. 1, the ultrasonic endo-probe 1 has a connector 4, a tubular member 5 and an ultrasonic transducer assembly 13 and a drive shaft 12. The tubular member 5 has an acoustic window 15 and a distal end cover 16 at its distal (head) end. The interior space inside the acoustic window 15 is filled with a liquid 14 for propagating ultrasonic waves such as water. The ultrasonic transducer assembly 13 is disposed in the liquid-filled interior space of the tubular member 5. The rear end portion 13a of the ultrasonic transducer assembly 13 is rotatably supported by a slidably supporting member (bearing) 17 which is fixed in the tubular member 5. The rear end of the ultrasonic transducer assembly 13 is connected to the drive shaft 12 and turned by the driving shaft 12. The ultrasonic transducer assembly 13 converts electric signals into ultrasonic waves and incoming ultrasonic waves reflected from surrounding tissues into electric signals.

The tubular member 5 has a metal tube 10 made of a superelastic metal and a resin cover 11 which covers the surface of the superelastic metal tube 10.

A superelastic metal means an alloy generally called a shape-memory alloy which shows a superelasticity at the body temperature (around 37° C.). Preferable superelastic alloys include Ti—Ni binary alloy consisting essentially of 49 to 58 atom percents of Ni (the balance of Ti), Cu—Zn binary alloy consisting essentially of 38.5 to 41.5 wt% of Zn (the balance of Cu), Cu—Zn—X ternary alloy obtained by replacing part of Cu—Zn alloy with 1 to 10 wt% of X (X=Be, Si, Sn, Al or Ga), and Ni—Ai binary alloy consisting essentially of 36 to 38 atom percents of Al (the balance of Ni). Of these alloys, Ti—Ni binary alloy is especially preferable. The mechanical property of Ti—Ni alloy can be changed as desired by replacing part of Ti—Ni alloy with 0.01 to 2.0 atom percents of X (X=Co, Fe, Mn, Cr, V, Al, Nb, Pd, B, etc.). Super elasticity here means the capability of a superelastic metal to recover almost its former shape at the temperature at which it is used after it is deformed (bent, elongated or compressed) to such a degree that an ordinary metal undergoes permanent deformation.

The superelastic metal tube 10 is equal to or less than 6 mm and more preferably within the range of 0.3 to 5.5 mm in outside diameter. The wall thickness of the superelastic metal tube 10 is within the range of 50 to 200 μm and more preferably 80 to 150 μm. The buckling strength (yield point when subjected to increasing stress) of the superelastic metal tube 10 is within the range of 5 to 200 kg/mm$^2$ and more preferably 8 to 180 kg/mm$^2$ (22° C.). There covering stress (yield point when the stress is decreasing) is within the range of 3 to 180 kg/mm$^2$ and more preferably 5 to 160 kg/mm$^2$ (22° C.).

Figure 4:
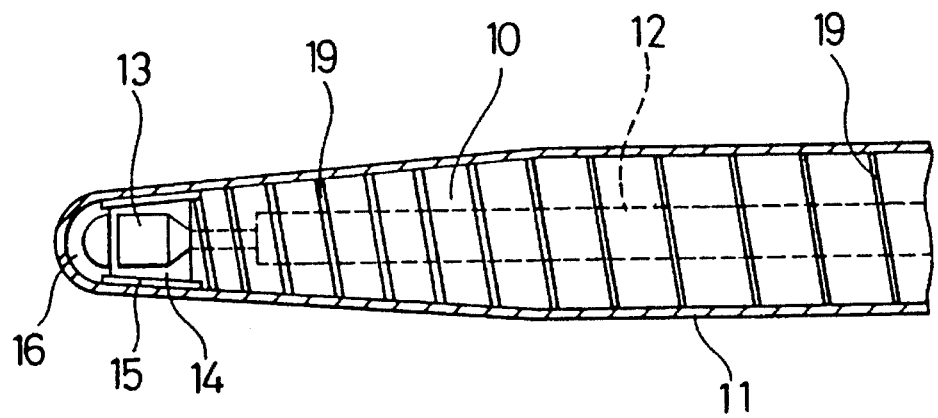
FIG. 4 is a sectional view of another embodiment of the ultrasonic endoprobe of this invention.

The structure of the superelastic metal tube 10 is not limited to that shown in FIG. 1. Another exemplary structure of the superelastic metal tube 10 is shown in FIG. 4. The superelastic metal tube 10 includes spiral slits 19 formed at a distal portion or zone thereof as in FIG. 4 and extending from the distal end toward the proximal end. Provision of the slits 19 ensures that the distal portion of the superelastic metal tube is a deformable portion which is more flexible than the remainder. More particularly, the distal portion of the superelastic metal tube 10 is flexible in that its side wall is deformable radially inward or outward.

As shown in FIG. 4, the spiral slit 19 is formed at such a width that the width is wider at the distal end and narrower at the proximal end of the slit region. Also preferably, the slit 19 is gradually decreased in width from the distal end toward the proximal end of the superelastic metal tube 10, or differently stated, gradually increased in width toward the distal end. The slit has the maximum width at the distal end of the metal tube 10. Then as one goes toward the distal end, the superelastic metal tube 10 is more flexible and deformable and the side wall is more deformable radially inward and outward. Preferably two to eight slits 19 are formed at approximately equal intervals. Also preferably, the slits 19 have a maximum width of about 0.05 to 0.5 mm at the distal end (as measured in a circumferential direction). The slit width is preferably about ⅙ to ½, more preferably about ⅓ to ¼ of the outer diameter of the metal tube.

Moreover, the spiral slit 19 is formed at such a pitch that the pitch is shorter at the distal end and longer at the proximal end of the slit region as shown in FIG. 4. Also preferably, the slit pitch is gradually increased from the distal end to the proximal end of the slit region. The slit width is not fixed since it is determined in accordance with the outer diameter of the outer tube or the like. Where the slit has a varying pitch, the pitch is preferably about 0.5 to 3.0 mm at the distal end and about 5 to 10 mm at the proximal end of the slit portion and an intermediate value at an intermediate region.

It is also acceptable that the pitch be continuously increased from the distal end toward the proximal end. Within this range, the metal tube distal portion is fully flexible and not broken or bent during operation. The extent of the distal portion of the metal tube where the slit is formed is determined by taking into account the length of the instrument or the like. Preferably the slit 19 has the varying pitch as described above and the varying width as described above.

The slit is formed in the superelastic metal tube by any of conventional techniques including laser machining (e.g., YAG laser), electric discharge machining, chemical etching, machining, and combinations thereof.

For the material of the resin cover 11, polyolefin elastomer (polyethylene, polypropylene, ethylene-propylene copolymer, etc.), polyvinyl chloride, ethylene-vinyl acetate copolymer, polyamide elastomer, polyurethane, thermoplastic resin such as fluororesin, synthetic rubber such as silicone rubber and natural rubber such as latex rubber can be used. It is preferable that the surface of the resin cover 11 has a high lubricity or wettability, which reduces the sliding friction and makes easier the insertion of the endoprobe 1 into a hollow organ or the body cavity of the living body. To increase the lubricity or wettability, the method which introduces an appropriate kind of functional group and coats with or fixes a high-molecular substance having a high lubricity or wettability can be used. For the high-molecular substance, hydrophilic polymers such as poly(2-hydroxyethyl metacrylate), polyhydroxyethylacrylate, hydroxypropyl cellulose, methyl vinyl ether-maleic anhydride copolymer, polyethylene glycol, polyacrylamide and poly(vinyl pyrrolidone can be used.

The outer diameter of the tubular member 5 (including the resin cover 11 as described above) is less than 7 mm and preferably within the range of 0.4 to 6 mm. The thickness of the resin cover 11 over the superelastic metal tube 10 is within the range of 0.005 to 0.3 mm and preferably 0.01 to 0.2 mm.

For the drive shaft 12, a coil of an outside diameter within the range of 0.1 to 4 mm, formed of a stainless steel wire or strip with a thickness or diameter within the range of 0.001 to 0.5 mm or a piano wire, may be used.

In the above embodiment, the tubular member 5 is entirely made of a superelastic metal tube with a resin cover. By thus forming the tubular member 5, the endoprobe 1 has a high capability of transmitting a turning force (torque) around the axis applied to the proximal end portion to the distal end portion (turnability or torque-transmissibility) as well as a high capability of transmitting a pushing force in the direction of the axis (pushability).

To further increase the elasticity of the distal end portion of the endoprobe 1, the distal end portion of the tubular member 5 may be made of a resin tube. The length of the distal end portion of the tubular member 5 to form of a resin tube is preferably within the range of about 1.0 to 2.0 mm. For the material of the resin tube, the aforementioned materials for the resin cover can also be used preferably.

Signal wires 18 for transmitting electric signals to and from the transducer assembly 13 are passed through the interior hollow space of the drive shaft 12. The signal wires 18 are connected to the rear end of the transducer assembly 13. The drive shaft 12 extends through the tubular member 5 and connector 4 and beyond the rear end of the connector 4. The proximal end of the drive-shaft 12 is connected to a coupler 34 of the motor unit 3 by plugging the connector 4 to the motor unit 3.

The drive shaft 12 is made by a coil. For the material of the drive shaft(coil)12, the aforementioned superelastic alloys end stainless steel such as precipitation hardening (especially semiaustenitic) stainless steel and mulaging stainless steel are preferable.

Figure 2:
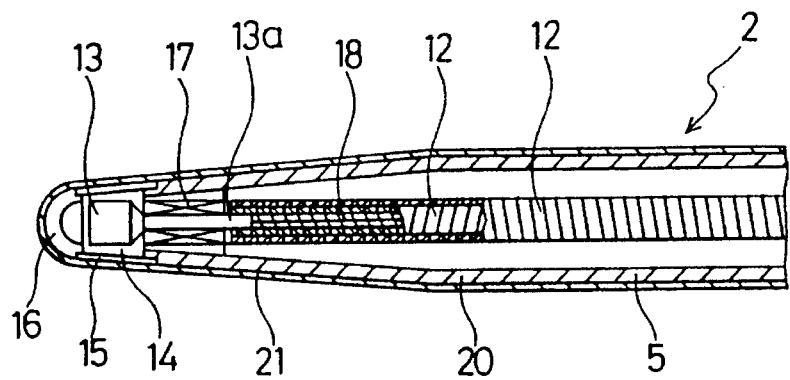
FIG. 2 is a sectional view of another embodiment of the ultrasonic endoprobe of this invention.
Figure 3:
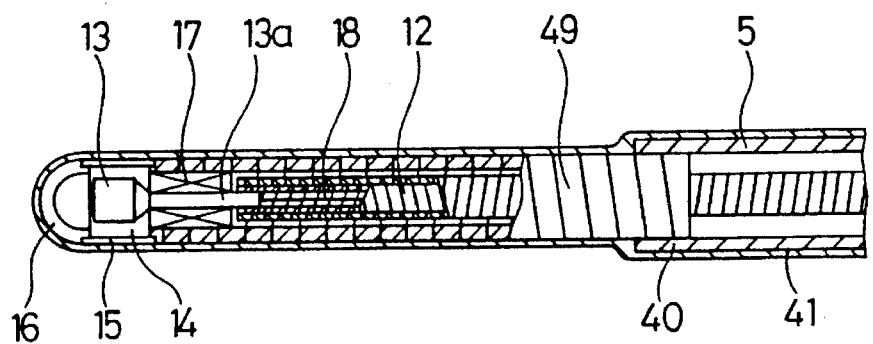
FIG. 3 is a sectional view of another embodiment of the ultrasonic endoprobe of this invention.

The number of layers of winding of the coil 12 is not limited to one. A multi-layer structure consisting of two or more layers is preferable in order to increase the turnability of the endoprobe as shown in FIGS. 1, 2 and 3. In such a multilayer structure, it is preferable to reverse the direction of winding alternately layer by layer. By this structure, the endoprobe has a high turnability or torque transmissibility along with a high pushability.

A drive shaft 12 as described above is encased in the interior hollow space of the ultrasonic endoprobe 1 or the tubular member 5. Signal wires 18 (signal line and ground line) are deposited in the interior hollow space of the drive shaft 12 as shown in FIG. 1. The wires are connected to electrical contacts 22a and 22b provided at the rear end surface of a plug member 23. An open end of the drive shaft 12 is closed by the plug member 23. The connector 4 is connected at an end- portion of the tubular member 5. The rear end portion of the drive shaft 12 is rotatably supported by a slidably supporting member (bearing) 21 which is fixed in the connector 4.

As shown in FIG. 5, the motor unit 3 comprises a motor 31, a gear 32, a rotating shaft 33, a coupler 34, and a rotary connector 35. When the motor 31, which is the driving power source, is rotating, the rotation is transmitted to the rotating shaft 33 via the gear 32. The rotation of the rotating shaft 33 is transmitted via the coupler 34 to the drive shaft 12, which rotates the ultrasonic transducer assembly 13. The rotary connector 35 slidably connects the wires extended from the coupler 34 in the rotating shaft 33 to the main unit 2 as described later. The electrical signal from the main unit 2 is transmitted to the transducer assembly 13 via the rotary connector 35, wires in the rotating shaft 33, coupler 34 and signal wires 18, and that from the transducer assembly 13 is transmitted to the main unit 2 in the reverse direction. The electric signal from the transducer assembly 13 is processed in the main unit 2. The known B mode technique is used for imaging by the ultrasonic endoprobe 1.

Another embodiment of the ultrasonic endoprobe of this invention is shown in FIG. 2. The same components as those of the first embodiment shown in FIG. 1 are designated by the same reference numbers, and the explanation of them is not given.

The ultrasonic endoprobe 2 of this embodiment has a distal end portion of the tubular member 5 formed so as to become gradually smaller in diameter toward the distal end. By thus tapering the distal end portion of the tubular member 5, the distal end portion is made more flexible and insertion of the endoprobe into a hollow organ or a body cavity or the living body becomes much easier, substantially without lowering the turnability or torque transmissibility or pushability.

Another embodiment of an ultrasonic endoprobe of this invention is shown in FIG. 3. The same components as those of the first embodiment shown in FIG. 1 are designated by the same reference numbers, and the explanation of them is not given.

The tubular member 5 of the ultrasonic endoprobe 3 of this embodiment is made of a superelastic metal tube 40 and a coil 49 made of a metallic material. The superelastic metal tube 40 and the coil of a metallic material 49 are bonded by welding or brazing, for example. An acoustic window 15 and a distal end cover 16 are attached at the distal end of the coil 49.

For the coil of a metallic material 49, a coil which has an outside diameter within the range of 0.2 to 4 mm and is formed of a stainless steel wire or strip within the range of 0.001 to 0.5 mm in diameter or thickness or a piano wire. By forming only the distal end portion of the tubular member 5 of a coil of a metallic material and forming the other portion of a superelastic metal tube, the entire tubular member 5 is made sufficiently thin in wall thickness and smaller in diameter and the distal end portion is made more flexible maintaining a high pushability and turnability and torque-transmissibility.

Although the above embodiments are all of the radial scan type, the ultrasonic endoprobe of this invention can be embodied in another scan type such as linear scan type or sector scan type.

Figure 6:
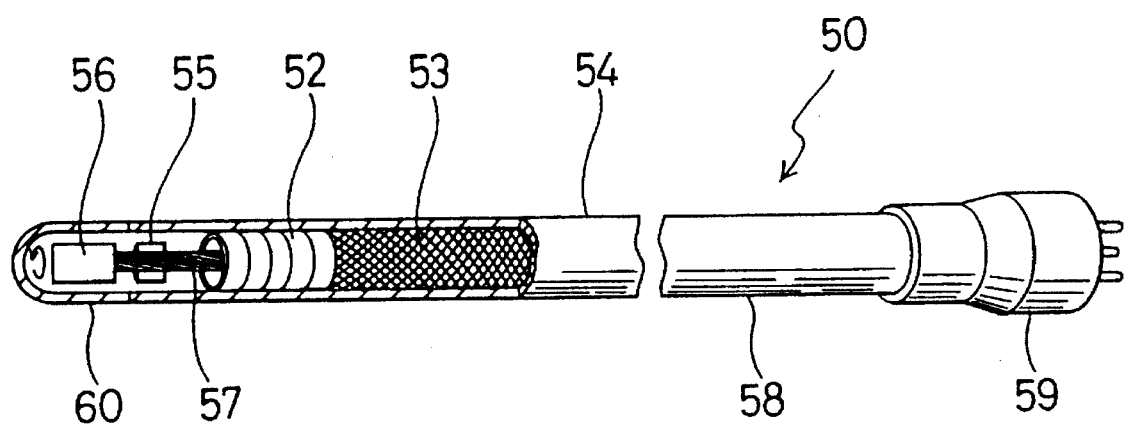
FIG. 6 is a sectional view of another embodiment of the ultrasonic endoprobe of this invention.

Next, another embodiment of the ultrasonic endoprobe of this invention shown in FIG. 6 is described.

The ultrasonic endoprobe 50 comprises the inner assembly which has an ultrasonic transducer assembly 56, a coil 52 and a braid 53 (braided wires) covering the almost entire surface of the coil 52; an outer cover 54 which covers the almost entire surface of the inner assembly; and a connector 59. The ultrasonic transducer assembly 56, which extends beyond the distal end of the coil 52, is housed by a distal end covering material 60.

A drive shaft 57 is put inside the coil 52. The distal end of the drive shaft 57 is connected to the rear end of the ultrasonic transducer assembly 56. The drive shaft 57 is rotatably supported by a bearing 55 fixed inside the outer cover 54 or the coil 52. The drive shaft 57 is driven to rotate the ultrasonic transducer assembly 56 in the direction shown by the arrow in FIG. 6 for radial scanning. The ultrasonic transducer assembly 56 converts electric signals into ultrasonic waves and incoming ultrasonic waves reflected from surrounding tissues into electric signals. Signal wires (not shown) are passed through the interior hollow space of the drive shaft 57. A connector 59 for the connection to an ultrasonic diagnostic apparatus as shown in FIG. 5 is provided at the proximal end 58 of the ultrasonic endoprobe 50.

The drive shaft 57 extends through the coil 52 and connector 59 and beyond the rear end of the connector 59. The proximal end of the drive shaft 57 is connected to a coupler 34 of the motor unit 3 by plugging the connector 59 to the motor unit 3.

The known B mode technique is used for imaging by the ultrasonic endoprobe.

The inside diameter of the coil 52 is within the range of 0.1 to 6 mm and preferably 0.3 to 3 mm. For the coil 52, a closely-wound coil formed of a strip with a width within the range of 0.05 to 1.0 mm and preferably 0.1 to 0.4 mm and a thickness within the range of 0.005 to 0.2 mm and preferably 0.01 to 0.5 mm or a wire with a diameter within the range of 0.01 to 0.5 mm and preferably 0.05 to 0.2 mm is used.

For the material of the coil 52, the aforementioned superelastic alloys and stainless steel such as precipitation hardening (especially semiaustenitic) stainless steel and mulaging stainless steel are preferable.

The number of layers of winding of the coil 52 is not limited to one. A multilayer structure consisting of two or more layers is preferable in order to increase the torque-transmissibility of the endoprobe 50. In such a multilayer structure, it is preferable to reverse the direction of winding alternately layer by layer. By this structure, the endoprobe 50 has a high turnability or torque-transmissibility along with a high pushability.

The braid 53 which covers the almost entire outside Surface of the coil 52 restrains the expansion and contraction of the coil 52. For the material of the braid 53, metallic materials (piano wire, stainless steel wire such as precipitation hardening (especially semiaustenitic) stainless steel and mulaging stainless steel, etc.), carbon fiber, and synthetic resin fibers such as aramid fiber and nylon (polyamide resin fiber) are preferable. The outside diameter of the wire or fiber is within the range of 0.005 to 0.2 mm and preferably 0.01 to 0.05 mm. The braid 53 is preferably formed by interweaving equal to or more than three and preferably eight strands. The braid 53 may consist of two or more layers. The multilayer braid 34 also increases the torque-transmissibility and pushability of the endoprobe.

The coil 52 and/or the braid 53 may be so formed that the cross section of their distal end portion is smaller, in order to make the distal end portion of the endoprobe more flexible. By thus forming the coil 52 and/or the braid 53, insertion of the endoprobe into a hollow organ becomes easier and the manipulatability of the endoprobe improves. The distal end portion of the coil 52 and the braid 53 may be tapered so as to become gradually smaller in outside diameter toward the distal end of the endoprobe. By thus tapering the coil 52 and the braid 53, insertion of the endoprobe into a hollow organ or body Dart, especially peripheral blood vessel, becomes easier.

The distal end cover 60 is within the range of 0.01 to 0.5 mm and preferably 0.02 to 0.2 mm in outside wall thickness. For the material of the distal end cover 60, thermoplastic resins with a good acoustic transmittance such as polyolefin rein, polyester resin and nylon resin can be used. The same material or the same kind of material as that of the outer cover 54 is preferable. The acoustic impedance (Z) of the distal end cover 60 is $0.8 \times 10_6$ to $4.0 \times 10_6$ kg/ms$^2$ and preferably $1.0 \times 10^6$ to $3.0 \times 10_6$ kg/ms$^2$.

The distal end cover 60 may be formed as a separate part from the outer cover 54 and attached to the distal end of the outer cover 54, or may be formed as an integrated part of the outer cover 54. Bonding with an adhesive agent or welding by ultrasonic waves or a laser beam may be used to attach the distal end cover 60 to the outer cover 54. The interior of the distal end cover 60 is filled with an appropriate liquid for transmitting acoustic waves such as water.

The rotating torque from the aforementioned motor unit 3 is transmitted to the ultrasonic transducer assembly 6 in the distal end cover 60. For the material of the drive shaft 57, superelastic alloys such as Ti—Ni binary alloys consisting essentially of 49 to 53 atom percents of Ni and the balance of Ti, Cu—Zn binary alloys consisting essentially of 38.5 to 41.5 wt% of Zn and the balance of Cu, Cu—Zn—X ternary alloys consisting essentially of 1 to 10 wt% of X (X=Be, Si, Sn, Al or Ga) and the balance of Cu, and Ni—Al binary alloys consisting essentially of 36 to 38 atom% of Al and the balance of Ni and stainless steel such as precipitation hardening (especially semiaustenitic) stainless steel and mulaging stainless steel are preferable. The drive shaft 57 is preferably a single wire or a stranded or non-stranded (bundled) wire of two or more strands.

For the material of the outer cover 54 which covers the almost entire outside surface of the braid 53, polyolefin resin (polyethylene elastomer, polypropylene elastomer, ethylene-propylene copolymer elastomer, etc.), polyester resin, nylon resin, polyvinyl chloride, ethylene-vinyl acetate copolymer, polyamide elastomer, polyurethane, thermoplastic resin such as fluororesin, synthetic rubber such as silicone rubber, and natural rubber such as latex rubber can be used. It is preferable that the surface of the outer cover 54 has a high lubricity or wettability. To increase the lubricity or wettability, it is preferable to introduce an appropriate kind of functional group into the outer cover 54 and coat the outer cover 54 with a high-molecular substance having a high lubricity or wettability, For the high-molecular substance, hydrophilic polymers such as poly(2-hydroxyethyl metacrylate), polyhydroxyethyl-acrylate, hydroxypropyl cellulose, methyl vinyl ether-maleic anhydride copolymer, polyethylene glycol, polyacrylamide and poly(vinyl pyrrolidone can be used.

The endoprobe 50 may be divided into the proximal portion including the connector and the distal portion including the ultrasonic transducer assembly (main body) and detachably attached to each other. By thus dividing the endoprobe and throwing away the main body after use, it becomes easier to make the endoprobe disposable.

Figure 7:
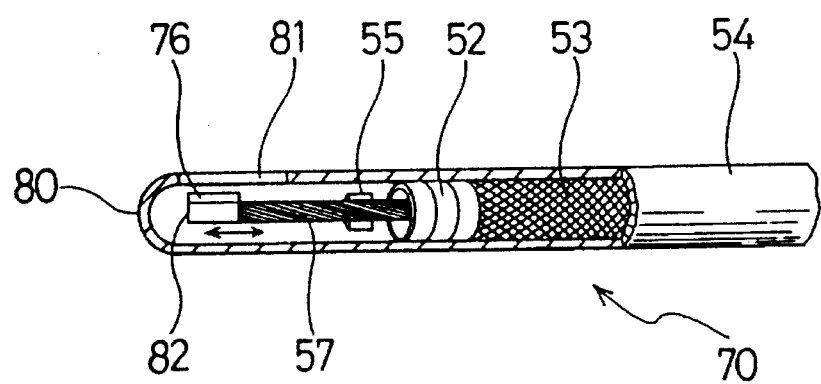
FIG. 7 is a sectional view of another embodiment of the ultrasonic endoprobe of this invention.

Next, another embodiment of the ultrasonic endoprobe of this invention shown in FIG. 7 is described. The same components as those of the embodiment shown in FIG. 6 are designated by the same reference numbers, and the explanation of them is not given.

The embodiment shown in FIG. 7 is an ultrasonic endoprobe of the linear scan type. The drive shaft 57 of this ultrasonic endoprobe 70 moves the ultrasonic transducer assembly 76 back and forth in the direction of the axis of the endoprobe as shown by the arrow in FIG. 7. The drive shaft 57 is supported by a sliding bearing 55. The sliding bearing 55 and the ultrasonic transducer assembly 76 are separated by a distance which allows the reciprocating motion of the ultrasonic transducer assembly 76. The ultrasonic transducer assembly 76 is provided with a back reflector 82. Signal wires for transmitting electric signals to and from the ultrasonic transducer assembly 76 are passed through the interior hollow space of the drive shaft 57 (not shown). An acoustic window 81 is provided in the distal end cover 80 at least at the part through which ultrasonic waves are emitted and received. The acoustic window 81 is formed of a material with a high ultrasonic transmittance, for example, a thermoplastic resin such as polyolefin resin, polyester resin or nylon resin.

By this structure, the ultrasonic endoprobe 70 of this embodiment linearly scans the aimed part of an organ or the body.

Linear scanning can also be performed by using a linear array of a plurality of ultrasonic transducers and exciting them in turn, instead of moving an ultrasonic transducer assembly back and forth in the direction of the axis of the endoprobe as described above.

Next, another embodiment of the ultrasonic endoprobe of this invention shown in FIG. 8 is described. The same components as those of the embodiment shown in FIG. 1 are designated by the same reference numbers, and the explanation of them is not given.

The difference between the ultrasonic endoprobe 90 of this embodiment and that shown in FIG. 1 is only the shape of the connector 4. The structure of the main body of the endoprobe is not limited to the one shown in FIG. 1. It may be the ones shown in FIGS. 2 to 7, and may also be the ones shown in FIGS. 10 to 13 described later. The intra-body ultrasonic diagnostic apparatus comprises an ultrasonic endoprobe 1, a main unit 2 and a motor unit 3.

The ultrasonic endoprobe 90 of this embodiment has a connector 4 whose outside diameter is equal to or less than that of the tubular member 5. The endoprobe 90 is used by being inserted into an endoscope, PTCA catheter or guiding catheter inserted in a hollow organ or part of the body or a loving body cavity beforehand. There are occasions when the endoscope or catheter being used needs to be advanced further toward the periphery. If the endoscope or catheter is difficult to be pushed in, it must be replaced with one of a smaller diameter. There are also occasions when the endoscope being used needs to be replaced with a catheter. In such cases, if the outside diameter of the connector 4 is greater than that of the tubular member 5 of the ultrasonic endoprobe and the inside diameter of the endoscope or catheter, the ultrasonic endoprobe must be pulled out along with the endoscope or catheter and inserted again into a new endoscope or catheter after the new endoscope or catheter is inserted.

By forming the outside diameter of the connector 4 equal to or smaller than that of the hollow tube 5, the endoscope or catheter alone can be pulled out leaving the ultrasonic endoprobe in the body. A new endoscope or catheter can be easily inserted into the body by pushing it on the ultrasonic endoprobe.

Figure 10A:
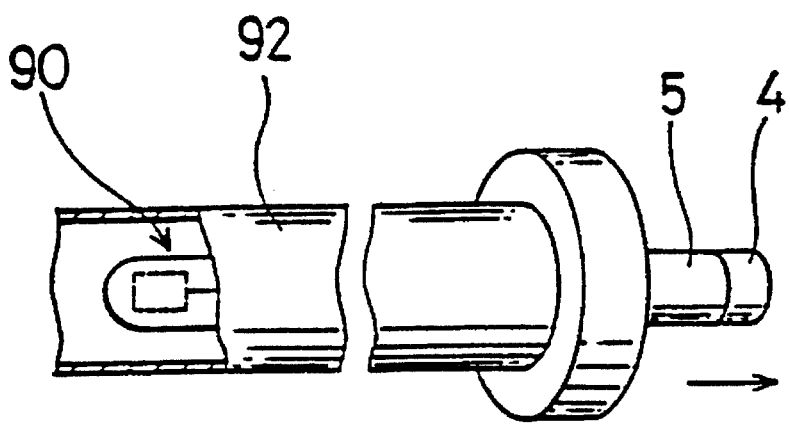
FIG. 10 (a) and (b) illustrate the procedure of the replacement of a catheter which is made possible by the ultrasonic endoprobe shown in FIG. 8.
Figure 10B:
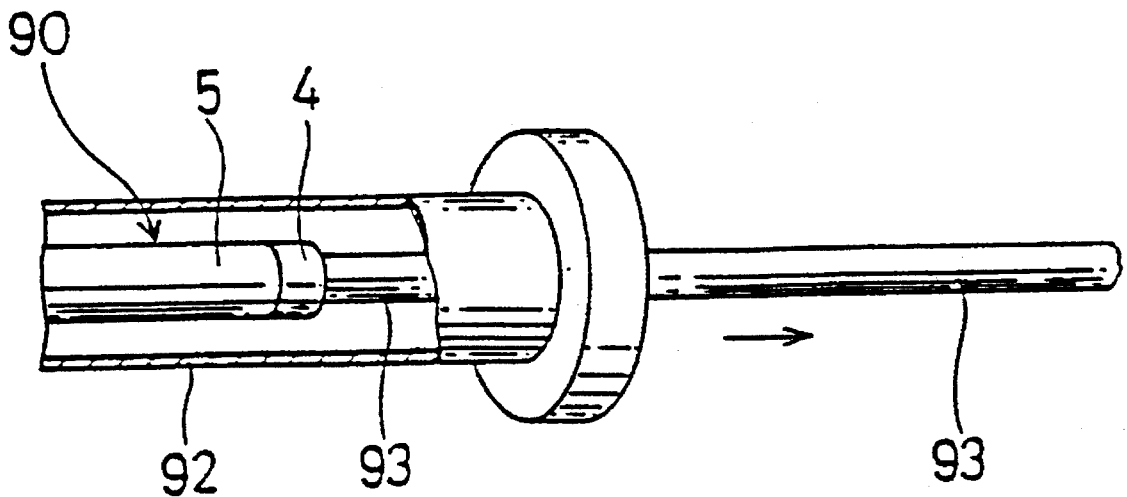

FIG. 10 (a) and (b) illustrate the procedure of the replacement of a catheter which is made possible by the ultrasonic endoprobe shown in FIG. 8.

The replacement of a catheter 92 (or endoscope) is performed by disconnecting the ultrasonic endoprobe 90 from the external unit (motor unit) 3, attaching a wire 93 longer than the catheter 92 to be pulled out to the connector 4 of the endoprobe 90; pulling back the catheter 92 on the wire 93 while firmly holding the wire 93 at the proximal portion and then taking it off the wire 93; putting a new catheter on the wire 93 while holding the wire 93 at the distal portion and then pushing the new catheter on the endoprobe 90 into the body; and detaching the wire 93 from the connector 4 after the insertion is completed.

FIG. 9 (a) is a longitudinal sectional view which shows the structure for connection of the ultrasonic endoprobe and the external unit shown in FIG. 8. FIG. 9 (b) is a cross sectional view of the connector of the ultrasonic endoprobe.

A drive shaft 12 as described above is encased in the interior hollow space of the ultrasonic endoprobe 90. Two conductors or signal wires (signal line and ground line) 18a and 18b are deposited on the surface of the drive shaft 12. These conductors 18a and 18b are connected to electrical contacts 84a and 84b provided at the rear end surface of the connector 4, respectively. These electrical contacts 84a and 84b are disposed so as to oppose to each other with a groove formed in the proximal end surface of the connector 4 between. The connector 4 is rotatably supported by a bearing 63 attached to the proximal end of the tubular member 5. Although the bearing 63 is a separate part, it may also be formed as an integrated part of the tubular member 5.

The external unit (motor unit) 3 has a receptacle 46 rotatably supported by a bearing 64. The receptacle 46 has a recessed opening for receiving the connector 4. A projection 68 is formed in the bottom of the recessed opening. Electric contacts 85a and 85b are slidably supported in the holes formed in the-bottom of the recessed opening. Signal wires 42 are connected to the electric contacts 85a and 85b. The electric contacts 85a and 85b are pressed forward on the rear end by springs 66. Springs 76 are provided on the cylindrical wall of the recessed opening.

When the connector 4 of the endoprobe is plugged into the receptacle 46, the connector 4 is secured to the receptacle 46 by the depressed springs 76. The electric contacts 84a and 84b of the connector 4 press the electric contacts 85a and 85b of the receptacle 46 against the springs 66 and come into steady contact with the electric contacts 85a and 85b. The projection 68 of the receptacle 46 fits into the groove 69 of the connector 4 and transmits the rotating force to the drive shalt 12.

The structure of the ultrasonic endoprobe of the invention is not limited to that shown in Figures. It is acceptable that the ultrasonic transducer has a reflector provided in front of or at the back of it and the reflector rotates together with said ultrasonic transducer. It is acceptable that some ultrasonic transducers are housed in the distal end portion of the tubular member and so arranged that scanning is performed by exciting these ultrasonic transducers in turn.

Figure 11:
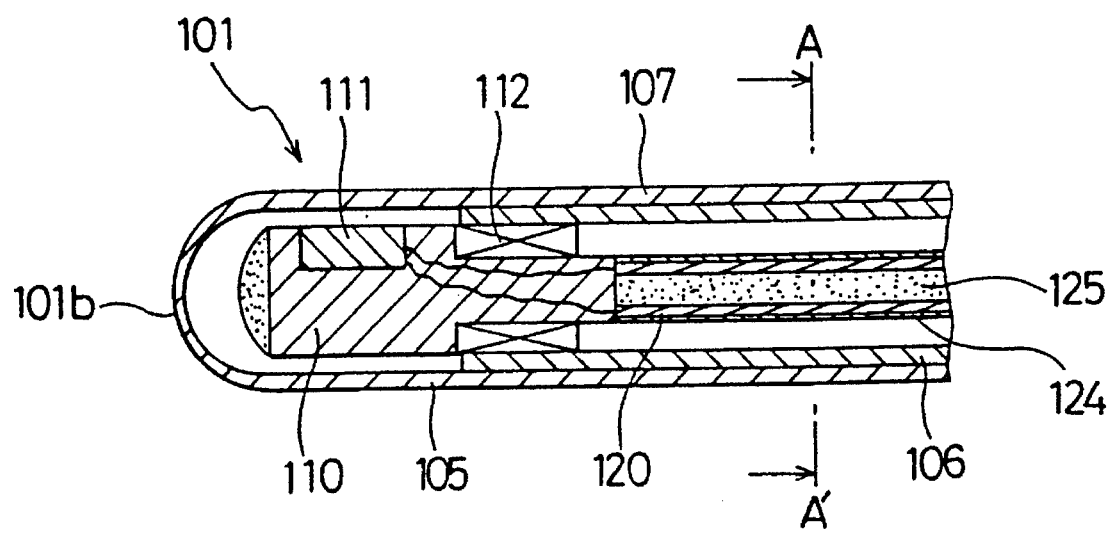
FIG. 11 is a sectional view of the distal end portion of the intra-body measurement catheter of this invention.
Figure 12:
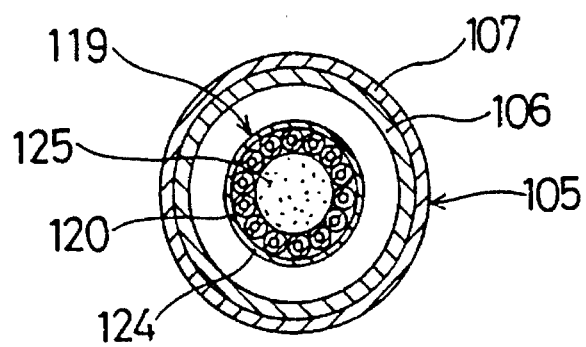
FIG. 12 is the sectional view along the A—A line in FIG. 11.
Figure 13:
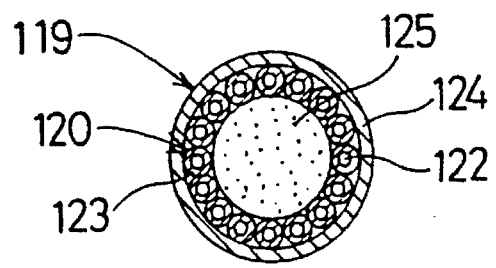
FIG. 13 is an enlarged sectional view of the inner shaft assembly of the intra-body measurement catheter of this invention shown in FIG. 11.

Next, the intra-body measurement catheter of this invention shown in FIGS. 11, 12 and 13 is described.

Figure 14:
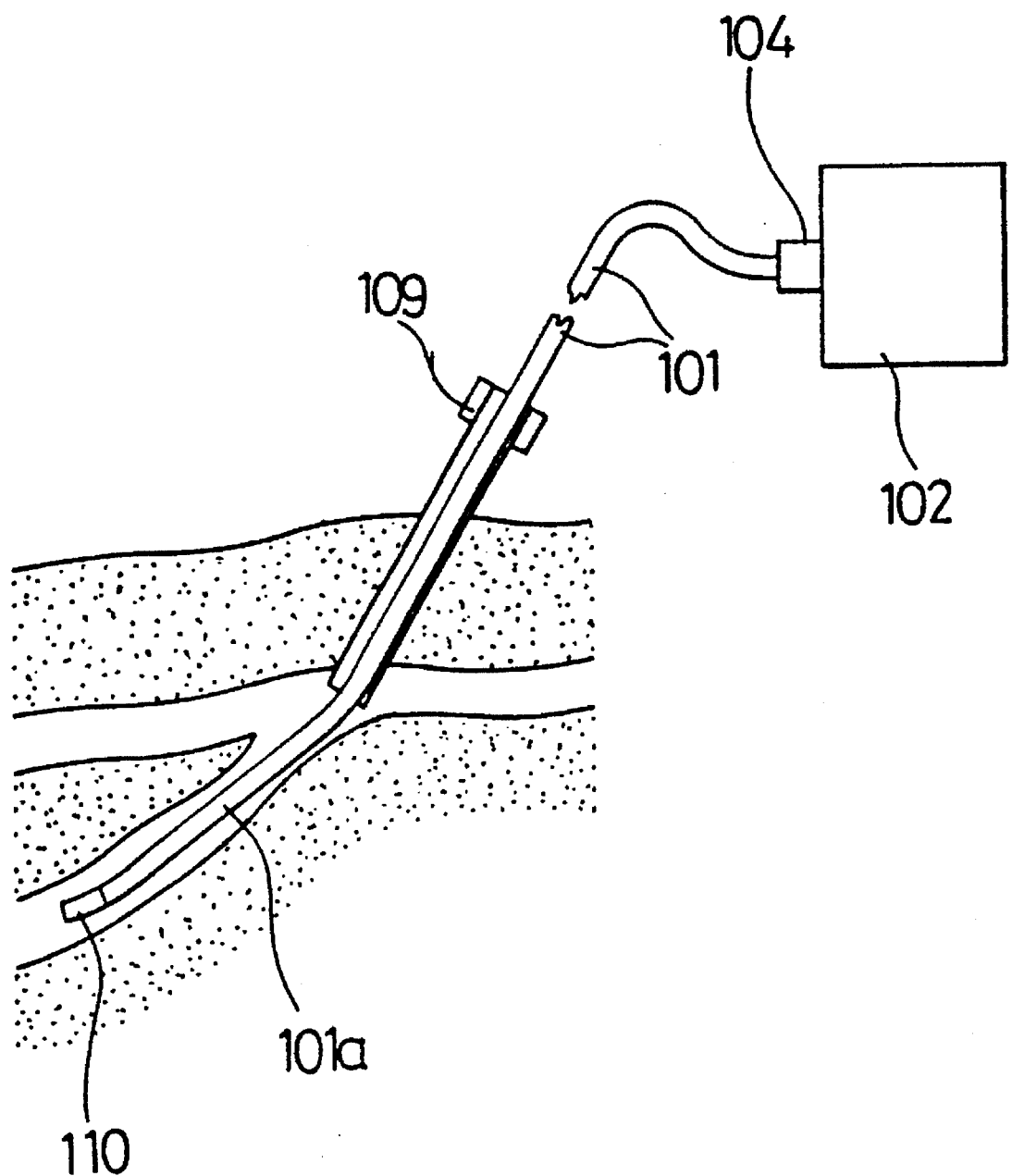
FIG. 14 illustrates the method of using the intra-body measurement catheter of this invention.

The intra-body measurement catheter 101 is connected to an external unit 102 by means of a connector 104 as shown in FIG. 14 to form an intra-body measurement apparatus. The external unit 2 has the function for processing the signal from the catheter and a driving mechanism for rotating the inner drive shaft of the catheter 101. The catheter 101, like in common angioraphy, is used by piercing an introducer 109 into the artery of a patient, inserting the catheter 101 into the blood vessel through the introducer 109, and positioning the distal end of the catheter at the intended part of the blood vessel as shown in FIG. 14.

The catheter 101 comprises a catheter tube 105, an inner shaft assembly 119, and a connector 104.

The catheter-tube 105 is formed of a tubular member 106 open at its distal end and a cover 107 which covers the outside surface of the tubular member 106 and has a closed distal end portion extending beyond the distal end of the tubular member 106. The tubular member 106 and cover 107 may be formed as a single component.

The tubular member 106 is formed of an superelastic alloy or a resin as described above. Ti—Ni superelastic alloy is preferable.

The structure of the tublar member 106 is not limited to that shown in FIG. 11. The tubular member 106 preferable includes spiral slits formed at a distal portion or zone thereof as shown in FIG. 4 and extending from the distal end toward the proximal end. The spiral slit is preferable formed at such a width that the width is wider at the distal end and narrower at the proximal end of the slit region. Also preferably, the spiral slit is formed at such a pitch that the pitch is shorter at the distal end and longer at the proximal end of the slit region as shown in FIG. 4. Also preferably, the slit pitch is gradually increased from the distal end to the proximal end of the slit region. Also preferably, the slit width is gradually decreased from the distal end to the proximal end of the slit region. It is also acceptable that the pitch be continuously increased from the distal end toward the proximal end. Preferably the slit has the varying pitch as described above and the varying width as described above.

For the material of the cover 107, synthetic resins such as polyolefin elastomer (polyethylene elastomer, polypropylene elastomer, ethylene-propylene copolymer elastomer, etc.), polyvinyl chloride, ethylene-vinyl acetate copolymer, polyamide elastomer, polyurethane, thermoplastic resin (fluororesin, etc.), silicone rubber, ultraviolet setting resin, urethane resin, acrylic resin, polyamide, and imide resin; synthetic rubbers such as silicone rubber; and natural rubber such as latex rubber can be used.

It is preferable that the surface of the cover has a high lubricity or wettability inherent to the resin material or imparted by a surface treatment. To increase the lubricity or wettability, the aforementioned method can be used.

In terms of the flexibility, torque-transmissibility, manipulatability, resistance to kinking, and diameter of the catheter, the outside diameter of the cover 107 (catheter) is preferably within the range of 0.3 to 6 mm; the wall thickness of the sheath is preferably within the range of 5 to 50 μm; and the wall thickness of the tubular member 106 is preferably within the range of 2 to 200 μm.

FIG. 12 is the sectional view along the A—A line in FIG. 11. FIG. 13 is an enlarged sectional view of the inner shaft assembly of the intra-body measurement catheter of this invention shown in FIG. 11.

The inner shaft assembly 119 includes a torque transmitting member (drive shaft) 125 encased in the catheter tube 105, a sensor assembly 110 attached to the distal end of the torque transmitting member 125, and electric conductors 121 for signal transmission (signal lines) bonded on the surface of the torque transmitting member 125 shown in FIGS. 12 and 13.

In this embodiment, an ultrasonic transducer 111 is used as the sensor of the sensor assembly 110. The sensor assembly 110 is protruded out of the distal end opening of the tubular member 106 and housed in the distal end portion of the sheath 107. The part of the sheath 107 around the sensor assembly 110 is made of a material with a high ultrasonic transmittance. The sheath 107 may be provided with an acoustic window as shown in FIG. 1.

An optical sensor (end of fiber optics, for example) can be used in place of or in addition to the ultrasonic transducer 111.

Further, a chemical sensor (big sensor such as pH sensor, $0_2$ sensor, $CO_2$ sensor or glucose sensor, for example) can be used as the sensor of the sensor assembly 110 by designing the catheter so that the sensor assembly 110 can be exposed in the body fluid.

The torque transmitting member 125 extends inside the catheter tube from the proximal end to the distal end. The signal lines 121, the number of which is equal to or greater than two, are bonded on the surface of the torque transmitting member 125 with an adhesive such as an acrylic adhesive. The torque transmitting member 125 is covered by a sheath 124.

The rear end portion of the sensor assembly 110 is slidably supported by a bearing member 112 fixed inside the tubular member 106. The rear end of the sensor assembly 110 is connected to the distal end of the torque transmitting member 125 as described above, and the sensor assembly 110 rotates along with the torque transmitting member 125.

The signal lines 121 transmits signals between the sensor assembly 110 and the external unit 102. The signal lines 121 are preferably wound on the torque transmitting member 125 helically in parallel with each other.

The torque transmitting member 125 has preferably a circular cross section and a tensile strength equal to or greater than 20 kgf/mm². The distal end portion of the torque transmitting member (about 5 cm or longer portion from the distal end 101b of the catheter 101) has preferably a sufficient flexibility. The preferable flexibility is such that the torque transmitting member can bend to 50 mm or smaller bending outside diameter. The bending outside diameter means such a diameter of the curvature of the torque transmitting member that the torque transmitting member can be bent by a force without kinking and recover to its former shape after the force is removed.

For the material of the torque transmitting member 125, metallic materials such as aforementioned superelastic alloys, stainless steel (precipitation hardening (especially semiaustenitic) stainless steel, mulaging stainless steel, etc.), high tensile strength steel, piano wire, Ni—Cr alloy) are preferable. Especially, the aforementioned superelastic alloys are preferable. The torque transmitting member is preferably a single wire or a stranded or non-stranded (bundled) wire of two or more strands.

The signal lines 121 consist of an electric conductor 122 and an insulator 123 covering the electric conductor 122. For the electric conductor 122, highly conductive metallic materials with a specific resistance equal to or smaller than $10^{-6}$ such as copper, copper-based alloys, silver, silver-based alloys, gold, and gold-based alloys are used. When the sensor of the sensor assembly 110 is an optical sensor, optical fibers made of methacrylic rein, for example, can be used for the signal lines 121.

For the insulator 123, resins with a specific resistance equal to or greater than $10^{-6}$ such as polyethylene, polyester, polyurethane, acrylic resin, polyimide, and polytetrafluorothylene can be used.

The sheath 124 is used to make the outside surface of the inner shaft assembly even and thereby the rotation of the inner shaft assembly smooth. Pot the material of the sheath 124, the aforementioned materials for the insulator 123 can be preferably used. Especially, tetrafluorothylene and acetal resin with a high slidability are preferably. To increase the slidability of the outside surface of the sheath 124, the sheath 124 may be coated with substances such as cellulose-related high molecular substances (hydroxypropyl cellulose, etc.), acrylamide high molecular substances (polyacrylamide, etc.), and polyethyleneoxide high molecular substances (polyethylene glycol, etc.).

The first ultrasonic endoprobe of this invention has an tubular member entirely or partly formed of a superelastic material as described above. Since a tubular member formed of a superelastic material can be made very thin in wall thickness maintaining a desired pushability, torque-transmissibility and turnability, this ultrasonic endoprobe has a very small diameter and a good manipulatability.

The second ultrasonic endoprobe of this invention has an tubular member formed of a composite member of a coil and a braid covering the almost entire outside surface of the coil and an outer cover covering the almost entire outside surface of the composite member. This ultrasonic endoprobe has a very small diameter, an improved flexibility, a high durability, and a high torque-transmissibility.

The intra-body measurement catheter also has a small diameter, a high flexibility, and a high torque-transmissibility.

We claim:

1. An ultrasonic endoprobe comprising:

a tubular member having an interior hollow space, the tubular member including a metal tube and a resin cover which covers an outer surface of said metal tube, said metal tube being provided with a spiral slit arrangement formed in a slit region at a distal portion of the metal tube, said spiral slit arrangement being formed with a pitch such that the pitch is smaller at a distal end of the slit region and greater at a proximal end of the slit region;

a drive shaft encased in the interior hollow space of said tubular member; and an ultrasonic transducer connected to said drive shaft.

2. The ultrasonic endoprobe of claim 1, wherein said metal tube is a superelastic metal tube.

3. The ultrasonic endoprobe of claim 1, wherein the distal portion of said tubular member has an outside diameter that gradually becomes smaller toward a distal end of the tubular member.

4. The ultrasonic endoprobe of claim 1, wherein said ultrasonic transducer is located outside a distal end of said metal tube.

5. The ultrasonic endoprobe of claim 1, wherein said tubular member has an acoustic window provided at a distal end of said tubular member, and said ultrasonic transducer is located near said acoustic window.

6. The ultrasonic endoprobe of claim 1, wherein an outside surface of said resin cover possesses high lubricity or wettability.

7. The ultrasonic endoprobe of claim 1, wherein said slit arrangement has a pitch that gradually increases from the distal end of the slit region to the proximal end of the slit region.

8. The ultrasonic endoprobe of claim 1, wherein said drive shaft is comprised of a coil and has an interior hollow space.

9. The ultrasonic endoprobe of claim 8, including signal wires connected to said transducer passing through said interior hollow space of said drive shaft.

10. The ultrasonic endoprobe of claim 1, wherein said ultrasonic transducer is attached to said drive shaft and is rotatably supported inside said tubular member by said drive shaft.

11. The ultrasonic endoprobe of claim 1, wherein said slit arrangement is comprised of a plurality of slits.

* * * * *

UNITED STATES PATENT AND TRADEMARK OFFICE
CERTIFICATE OF CORRECTION

PATENT NO. : 5,546,947
DATED : August 20, 1996
INVENTOR(S) : Hiroyuki YAGAMI, et al.

It is certified that error appears in the above-indentified patent and that said Letters Patent is hereby corrected as shown below:

In Column 3 line 37 delete "Ai" and insert --Al--.

In Column 5, line 31, delete "end" and insert --and--.

In Column 7, line 32, delete "Surface" and insert --surface--.

In Column 7, line 55, delete "Dart" and insert --part--.

In Column 7, line 64, delete "$0.8x10_6$" and insert --$0.8x10^6$--.

In Column 7, line 64, delete "$4.0x10_6$" and insert --$4.0X10^6$--.

In Column 7, line 65, delete "$3.0X10_6$" and insert --$3.0X10^6$--.

In Column 10, line 19, delete "the-bottom" and insert --the bottom--.

In Column 10, line 32, delete "shalt" and insert --shaft--.

In Column 10, line 49, delete "angioraphy" and insert --angiography--.

In Column 11, line 58, delete "big sensor" and insert --biosensor--.

In Column 12, line 50, delete "Pot" and insert --For--.

Signed and Sealed this

Twenty-first Day of January, 1997

Attest:

BRUCE LEHMAN

*Attesting Officer*  *Commissioner of Patents and Trademarks*